United States Patent
Peipsi

(10) Patent No.: US 9,808,158 B2
(45) Date of Patent: Nov. 7, 2017

(54) DEVICE AND METHOD FOR THE NON-INVASIVE MEASUREMENT OF STATE OF TENSION, BIOMECHANICAL AND VISCOELASTIC PROPERTIES OF SURFACES OF SOFT BIOLOGICAL TISSUES

(71) Applicant: MYOTON AS, Tallinn (EE)

(72) Inventor: Aleko Peipsi, Tallin (EE)

(73) Assignee: MYOTON AS, Tallinn (EE)

( * ) Notice: Subject to any disclaimer, the term of this patent is extended or adjusted under 35 U.S.C. 154(b) by 0 days.

(21) Appl. No.: 14/394,153

(22) PCT Filed: Apr. 12, 2013

(86) PCT No.: PCT/EP2013/057732
§ 371 (c)(1),
(2) Date: Oct. 13, 2014

(87) PCT Pub. No.: WO2013/156415
PCT Pub. Date: Oct. 24, 2013

(65) Prior Publication Data
US 2015/0038879 A1 Feb. 5, 2015

Related U.S. Application Data

(60) Provisional application No. 61/624,437, filed on Apr. 16, 2012.

(51) Int. Cl.
*A61B 5/00* (2006.01)
*B06B 1/04* (2006.01)
(Continued)

(52) U.S. Cl.
CPC ............ *A61B 5/0051* (2013.01); *A61B 5/442* (2013.01); *A61B 9/00* (2013.01); *B06B 1/04* (2013.01);
(Continued)

(58) Field of Classification Search
CPC ......... A61B 5/0051; A61B 9/00; A61B 5/442; A61B 2019/464; G01N 3/317; G01N 2203/0094; G01N 2203/0089; B06B 1/04
See application file for complete search history.

(56) References Cited

U.S. PATENT DOCUMENTS 5,277,200 A 1/1994 Kawazoe et al.
5,706,815 A * 1/1998 Sarvazyan ........... A61B 5/0051
600/438

(Continued)

FOREIGN PATENT DOCUMENTS

JP 61-181438 8/1986

OTHER PUBLICATIONS

Internet Archive, webpage "MyotonPRO Device", Apr. 12, 2012. Retrieved from <https://web.archive.org/web/20120412222044/http://www.myoton.com/en/Technology> on Feb. 2, 2016.*

(Continued)

*Primary Examiner* — David J McCrosky
(74) *Attorney, Agent, or Firm* — Heslin Rothenberg Farley & Mesiti P.C.; Victor A. Cardona, Esq.

(57) ABSTRACT

A device and method for the non-invasive measurement of state of tension, biomechanical and viscoelastic properties of surfaces of soft biological tissues includes electronic, digital and mechanical elements and sensors, and a testing end. The elements within the housing can subject the testing end to a mechanical impulse force, and can sense the movement of the testing end. The testing end has a contact surface which can be adhered to the surface of the soft biological tissue, and subjected to a mechanical force in a direction parallel to the surface.

12 Claims, 1 Drawing Sheet

(51) Int. Cl.
*A61B 9/00* (2006.01)
*G01N 3/317* (2006.01)
*A61B 90/00* (2016.01)

(52) U.S. Cl.
CPC ........ *G01N 3/317* (2013.01); *A61B 2090/064* (2016.02); *G01N 2203/0089* (2013.01); *G01N 2203/0094* (2013.01)

(56) References Cited

U.S. PATENT DOCUMENTS

| | | | |
|---|---|---|---|
| 6,132,385 A * | 10/2000 | Vain | A61B 5/103 600/553 |
| 2001/0031934 A1 | 10/2001 | Sarvazyan et al. | |
| 2005/0065426 A1 | 3/2005 | Porat et al. | |
| 2005/0113691 A1 | 5/2005 | Liebschner | |
| 2008/0173104 A1 | 7/2008 | German | |
| 2011/0054355 A1 | 3/2011 | Hunter et al. | |
| 2011/0144541 A1 * | 6/2011 | Kuroda | A61B 5/0053 600/587 |
| 2011/0172565 A1 | 7/2011 | Shih et al. | |
| 2015/0005679 A1 * | 1/2015 | Becse | A61N 1/0476 601/15 |

OTHER PUBLICATIONS

Bizzini, et al. "Reliability of a new, hand-held device for assessing skeletal muscle stiffness." Clinical Biomechanics 18.5 (2003): 459-461.*

Zinder, et al. "Reliability, validity, and precision of a handheld myometer for assessing in vivo muscle stiffness." J Sport Rehabil 6 (2011): 1-8.*

International Search Report for PCT/EP2013/057732 dated Aug. 8, 2013.

* cited by examiner

DEVICE AND METHOD FOR THE NON-INVASIVE MEASUREMENT OF STATE OF TENSION, BIOMECHANICAL AND VISCOELASTIC PROPERTIES OF SURFACES OF SOFT BIOLOGICAL TISSUES

FIELD OF INVENTION

The present invention relates to the field of medical diagnostic technologies, more precisely to the field of methods and devices for measurement of biomechanical and viscoelastic properties of biological surfaces, including but not limited to the skin.

BACKGROUND OF THE INVENTION

Human skin provides the body with a flexible barrier to the exterior environment through a highly integrated layered structure consisting of epidermis, dermis and subcutaneous tissues. Each layer has its own specific structure and functions. Mechanical behavior of the human skin is complex and well known to exhibit nonlinear and time-dependent mechanical behavior.

Soft biological tissues can be characterized by the state of tension, biomechanical and viscoelastic properties. Many attempts have been made to measure the biomechanical and viscoelastic properties of surfaces of soft biological tissues, for example human skin. The principal problem is how to evaluate human skin objectively, and to obtain numerical values, non-invasively, painlessly, quickly, and cost effectively, without causing the changes of the tissue being measured.

The US patent application US2011/0319792A1 describes a testing device for measuring biomechanical properties of skin for use by a surgeon, which has a force measurement device measuring the applied force, and a displacement measurement device measuring corresponding induced movement at a set of locations. The described testing device is not entirely satisfactory for the following reasons:

- Long duration of measurement process, which may influence the numerical value of the measured parameter;
- Only one parameter is measured, which is insufficient for objective characterization of the soft biological tissue;
- The measurement process requires use of a flexible articulated arm which is a restricting factor as regards its ease of use, making the measurement process complicated and requiring long preparation;
- The flexible articulated arm may allow measurements to be made only at certain angles of the measurement surface to the gravity vector;
- The solution is difficult to use objectively in micro- or zero gravity, which is essential for manned space flight missions.

BRIEF DESCRIPTION OF THE INVENTION

The aim of the present invention is to provide a solution for measuring surfaces of soft biological tissue with elastic properties, including but not limited to the skin, in real time, at any angle of orientation of the surface to the gravitation field, non-invasively, painlessly, quickly, cost effectively and without causing changes to the tissue being measured.

According to the present invention there is therefore provided a device for measurement of biomechanical and viscoelastic properties of a surface of a soft biological tissue with elastic properties, the device comprising a housing comprising electronic, digital and mechanical elements and sensors, characterized in that the device also comprises a testing end with a contact surface which can be adhered to the surface of the soft biological tissue, and subjected to a mechanical force in a direction parallel to the surface.

The electronic, digital and mechanical elements and sensors are adapted to subject the testing end to a mechanical impulse in a direction parallel to the surface, and also to measure the displacement of the testing end that results from the mechanical impulse. The displacement may be determined from measurements of acceleration. The mechanical impulse is applied after application of a preset pre-tension to the surface of the soft biological tissue, which ensures that the mechanical impulse is applied while the surface is under tension and can therefore undergo oscillation. The mechanical impulse is applied parallel to the surface so that deeper layers of the biological tissue are not significantly involved in the oscillation.

The contact surface may be of area at least 20 $mm^2$, and preferably at least 50 $mm^2$, and may be circular or oval, although other shapes are possible. For example it may be a circular plate of diameter 8 mm (area 50.2 $mm^2$) or of diameter 10 mm (area 78.5 $mm^2$), or of diameter 12 mm (area 113 $mm^2$). If the contact surface is too small, or if it has corners, then the mechanical impulse may generate excessively high local stresses; but if the contact surface is too large, then it prevents the device from being used to measure skin properties over a small area.

The electronic, digital and mechanical elements may optionally include a gravitational sensor, and a feedback circuit to ensure that the preset pre-tension and the mechanical impulse have values which are unaffected by the orientation of the housing relative to the gravitational field.

An important advantage of the present method and technical solution is that the mechanical impulse and subsequent registration of the tissue response is very short (less than 400 ms) so it doesn't influence the numerical values of the parameters being measured. The present invention lies in the design of testing end and in the combination of said testing end with a device (for example myometer Myotonpro™ www.myoton.com or similar devices) for subjecting an elastic biological surface to a short-term external mechanical impulse with quick release under constant pre-tension where the response to the impulse is subsequently registered by an accelerometer in the form of acceleration curve. In the present invention the mechanical impulse is applied parallel to the surface of the soft biological tissue. Deeper layers of soft biological tissues (eg superficial skeletal muscles) are not involved in the oscillation.

The device's construction and its firmware enable it to achieve repeatable and reliable measuring results. The device being used in this invention and its original testing end was designed for measuring deeper layers of soft biological tissues (eg. Superficial skeletal muscles and muscle tendons) but was not suitable for measuring of surfaces of soft biological tissues eg. Human skin.

The present invention comprises the testing end which makes possible to measure surfaces of soft biological tissues without involving deeper layers. The testing end is easy to attach to the device. In order to conduct the measurements with the present invention the device doesn't need any calibration or different settings.

The device has been designed for the non-invasive measurement of superficial soft biological tissue. The device may comprise a gravity-compensating system for its mechanism which allows it to take measurements at different angles (0° to 360°) to the Earth's gravitational field as well as in zero gravity, reproducibly and repeatedly, independently, portably, non-invasively and painlessly, cost-effectively, and quickly.

From the measured acceleration curve the device calculates the following parameters.
State of Tension:
1. F—Natural oscillation frequency [Hz];
Biomechanical Properties:
2. D—Logarithmic Decrement of natural oscillation, characterizing Elasticity;
3. S—Dynamic Stiffness [N/m];
Viscoelastic Properties:
4. C—Creep (Deborah number), calculated as the ratio of mechanical stress relaxation time to the deformation time;
5. R—Mechanical Stress Relaxation Time [ms].

The present invention also provides a method of measuring biomechanical and viscoelastic properties of a surface of a soft biological tissue with elastic properties, using a device comprising a housing comprising electronic, digital and mechanical elements and sensors, and a testing end with a contact surface which can be adhered to the surface of the soft biological tissue, the method comprising adhering the contact surface of the testing end to the surface of the soft biological tissue, and subjecting the testing end to a mechanical force in a direction parallel to the surface while monitoring the resulting acceleration of the testing end.

The method of measuring comprises the recording of the damped natural oscillation of soft biological tissue in the form of an acceleration graph and the subsequent simultaneous computation of the above given parameters associated with the tissue being measured. The method of present invention is objective, safe, non-invasive, painless, quickly applicable and cost-effective.

The measuring process of the surfaces of soft biological tissues with elastic properties comprises the following steps:
1. Constant longitudinal pre-tension is applied to the surface being measured. Constant pre-tension is necessary to achieve consistent and repeatable surface longitudinal oscillation at different angles to the gravity vector.
2. After pre-tension the longitudinal mechanical impulse with quick-release is exerted by the device at constant mechanical force.
3. The surface responds to the exterior mechanical impulse by a damped natural oscillation. The co-oscillation of the surface and testing end are recorded by an accelerometer in the form of an acceleration graph.
4. From the raw signal obtained above in step 3, the low and high frequencies that are not characteristic to the soft biological tissue's natural oscillation are then filtered out.
5. On the basis of the processed oscillation signal, numerical values describing state of tension of the surface being measured as well as its biomechanical and viscoelastic properties are then calculated.

The longitudinal mechanical impulse exerted to the surface is of short duration and involves minimal mechanical force, hence it does not cause residual mechanical deformation nor neurological reaction of the subcutaneous tissues being evaluated.

Definitions of Parameters
State of Tension
F—Oscillation Frequency [Hz] indicates the state of intrinsic tension of the tissue.
Biomechanical Properties
D—Logarithmic Decrement of a natural oscillation indicates the elasticity of tissue being measured, as it corresponds to the dissipation of mechanical energy in the tissue during a damped oscillation. Elasticity is the biomechanical property that characterizes the ability of the tissue to recover its initial shape after removal of the force or deformation; if the material were perfectly elastic, with no dissipation of energy, the decrement would be zero, and the larger the decrement then the less elastic is the material.
S—Dynamic Stiffness [N/m] is the biomechanical property that characterizes the tissue's ability to resist a force of deformation. The term dynamic stiffness originates from the dynamic measurement method. The inverse of stiffness is compliance.
Visco-Elastic Properties
C—Creep is the gradual elongation over time when placed under a constant tensile stress. This can be characterised by calculating the ratio of the mechanical stress relaxation time and the time to cause maximum deformation.
R—Mechanical Stress Relaxation Time [ms] is the time taken for the tissue that has been deformed to return to its initial shape after removal of the force of deformation.

BRIEF DESCRIPTION OF THE DRAWINGS

The present invention is explained more precisely with references to the accompanying drawings, where.

DETAILED DESCRIPTION OF THE INVENTION

Figure 1:
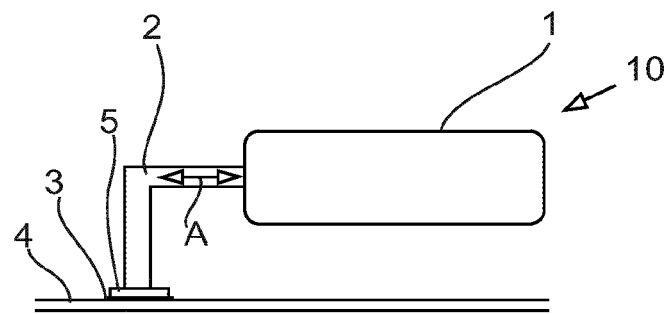
FIG. 1 shows a general schematic view of the device of the present invention.

Referring to FIG. 1, a device 10 according to the present invention comprises an L-shaped testing end 2, a contact substance 3, and a body or housing 1 containing electronic, digital and mechanical elements and means, including sensors for governing the measuring process and for calculating parameters of a surface 4 of a soft biological tissue with elastic properties. The testing end 2 defines a contact surface 5 which is held parallel to the surface 4, and is also parallel to the direction of the mechanical impulse, indicated by the arrow A.

The contact substance 3 may be a double-sided adhesive tape, for example in the form of a circular patch, or alternatively may be a skin adhesive. If the contact substance 3 is a circular patch of double-sided adhesive tape, it may be of slightly larger diameter than the contact surface 5. For example the contact surface 5 may be a circle of diameter 10 mm, while the circular patch of double-sided adhesive tape may be of diameter 12 mm. This ensures that it is not necessary to locate the contact surface 5 exactly concentric with the circular patch.

Figure 2:
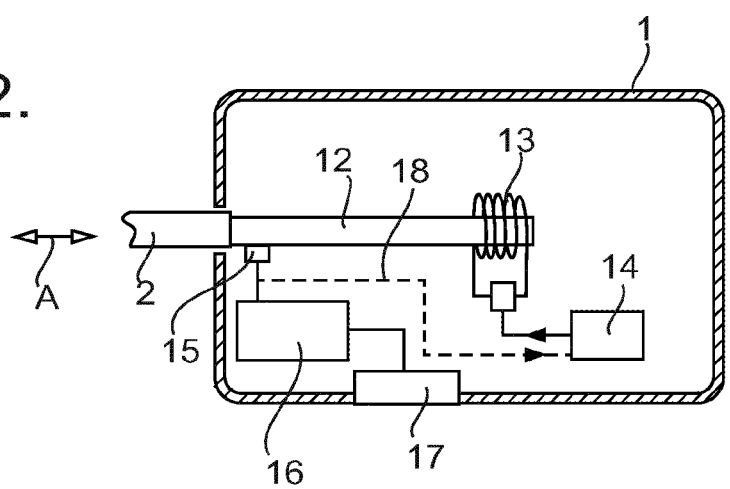
FIG. 2 shows a schematic view of components within the device of FIG. 1.

Referring now to FIG. 2, this shows schematically the components within the housing 1. Within the housing 1 the end of the testing end 2 is fixed to the end of an actuator shaft 12. The actuator shaft 12 is supported so it is free to move axially without friction, as indicated by the arrow A. For example the actuator shaft 12 may be supported by leaf springs (not shown). The other end of the actuator shaft 12 is provided with a non-contact electromagnetic force actuator 13 which can provide a controlled force axially to the actuator shaft 12. The force provided by the actuator 13 is controlled by a control circuit 14. An accelerometer 15 is mounted on the actuator shaft 12, and signals from the accelerometer 15 are provided to a signal analysis unit 16. In this example the signal analysis unit 16 is connected to a digital display 17.

Hence, referring again to FIG. 1, once the contact surface 5 has been adhered to the surface 4, the force actuator 13 is actuated initially to provide a preset pre-tension to the surface 4. Once the surface 4 has been subjected to this pre-tension, the force actuator 13 is arranged to apply a brief mechanical impulse, while continuing to apply the pre-tension force to the actuator shaft 12. The mechanical impulse has a duration less than 25 ms, for example 10 ms or 15 ms. Hence the actuator shaft 12, along with the testing end 2, is then free to oscillate along with the portion of the surface 4 which is adhered to the contact surface 5. After application of this mechanical impulse, the damped oscillation is monitored for up to 400 ms.

For connecting the measurement point on the surface 4 with the testing end 2, the contact substance 3 is attached either to the contact surface 5 or to the surface 4. The contact surface 5 of the testing end 2 is in touch with the surface 4 through contact substance 3, which enables firm connection between the testing end 2 and the surface 4 being measured.

To conduct the measurement, the testing end 2 is placed on the surface 4 being measured, the longitudinal mechanical impulse is applied, and the subsequent natural oscillation is recorded in the form of an acceleration curve with the data from the accelerometer 15. The natural oscillation of the surface 4 is registered by the accelerometer 15, and the device 10 hence measures the state of tension, biomechanical and viscoelastic properties.

The method for determining the biomechanical and viscoelastic properties of human skin, where human skin constitutes the surface 4, comprises the following steps.

The testing end 2 is placed at the measurement point on the surface 4 being measured. The device 10 is moved towards to the measurement point until the correct position of the measurement mechanism in the device 10 and required pre-tension is achieved. As soon as the correct position is achieved, the device 10 subjects the surface 4 to a longitudinal mechanical impulse of preset force. After the mechanical impulse the device 10 records the surface response in the form of an acceleration curve.

The parameters of state of tension, biomechanical and viscoelastic properties are then simultaneously calculated by the signal processing unit 16. The results may be displayed on a LCD screen of the digital display 17 of the device 10. Additionally or alternatively the data may be transmitted to an external device such as a portable computer.

Figure 3:
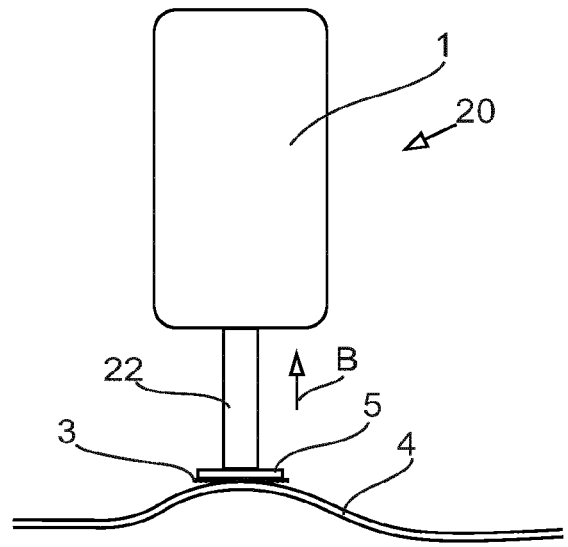
FIG. 3 shows a schematic view of a different mode of use of the device of FIG. 2.

Referring now to FIG. 3 there is shown an alternative way of measuring some properties of the surface 4 of a soft biological tissue, for example human skin, without involving deeper layers below the surface. This uses a device 20 which incorporates the housing 1 as described above, but in this case it is connected to a straight testing end 22. The testing end 22 defines a contact surface 5 which is connected and adhered to the surface 4 by a contact substance 3, in the same way as described above in relation to FIG. 1.

In use of the device 20, the contact surface 5 is adhered to the surface 4, and the electromagnetic force actuator 13 provides a quick mechanical impulse pulling the contact surface 5 away from the soft biological tissue, as indicated by the arrow B, and so deforming the surface 4 (as shown). The data from the accelerometer 15 can then be used to determine the displacement of the surface 4 from its original position, from which the elasticity of the surface can be deduced.

The preferred mode of operation is with the surface 4 horizontal, as shown in FIGS. 1 and 3, and with the device 10 or 20 above the surface 4. Where it is necessary to take measurements on surfaces 4 that are not horizontal, it is desirable to ensure that the pre-tension force and the mechanical impulse force are not altered as a result of the effect of gravity. Referring now to FIG. 2, the accelerometer 15 is arranged to measure the acceleration of the actuator shaft 12 (and so the testing end 2 or 22) parallel to the axis of the actuator shaft 12. Consequently, if the housing 1 is inclined from the horizontal, the accelerometer 15 provides a signal indicative of the angle of tilt of the housing 1 from the horizontal. As indicated by the broken line 18 the signals from the accelerometer 15 may be fed back to the control circuit 14, in order to compensate for this inclination from the horizontal.

The invention claimed is:

1. A device for measurement of biomechanical and viscoelastic properties of skin of a soft biological tissue with elastic properties, the device comprising:
    a housing including an actuator shaft provided with an actuator, and an accelerometer;
    a testing end with a contact surface configured for adhering to a surface of the skin of the soft biological tissue, the testing end configured to be subjected to a mechanical force along an axis of movement of the testing end in a direction parallel to the surface of the skin by actuation of the actuator, the accelerometer being mounted to the actuator shaft so as to move along with the testing end, and arranged to record acceleration of the testing end, the testing end being shaped such that the contact surface extends in a plane that is parallel to the axis of movement of the testing end,
    wherein the actuator is arranged to subject the testing end to a force such that the skin is subjected to a pre-set tension parallel to the axis of movement of the testing end, and then to apply a brief mechanical impulse parallel to the axis of movement of the testing end, while continuing to apply the pre-tension force, and wherein after the application of the brief mechanical impulse the resulting damped natural oscillation is recorded, as an acceleration curve, with data from the accelerometer; and
    a signal processing unit for performing signal processing on the data from the accelerometer during the damped natural oscillation to obtain values of the biomechanical and viscoelastic properties of the skin.

2. A device as claimed in claim 1 wherein the contact surface has an area from 20 mm$^2$ to 113 mm$^2$.

3. A device as claimed in claim 1 wherein the contact surface is circular or oval.

4. A device as claimed in claim 1, further comprising a gravitational sensor and a feedback circuit for ensuring that the preset pre-tension and the brief mechanical impulse, in operation of the device, are unaffected by orientation of the housing relative to a gravitational field.

5. A device as claimed in claim 1 wherein the testing end is L-shaped.

6. A device as claimed in claim 1, further comprising a control circuit, wherein the accelerometer is arranged to provide a signal indicative of orientation an inclination of the housing from a horizontal axis to the control circuit to compensate for the inclination from the horizontal axis.

7. A method of measuring biomechanical and viscoelastic properties of skin of a soft biological tissue with elastic properties with a device comprising: a housing including an actuator shaft provided with an actuator, and an accelerometer; and a testing end with a contact surface configured for adhering to a surface of the skin of the soft biological tissue, the testing end being movable along an axis of movement of the testing end in a direction parallel to the surface of the skin by actuation of the actuator, the testing end being shaped such that the contact surface extends in a plane that is parallel to the axis of movement of the testing end, the accelerometer being mounted to the actuator shaft so as to move along with the testing end, the method comprising the following steps:

placing the contact surface of the testing end on a measurement point on the surface of the skin being measured;

adhering the contact surface to the surface of the skin of the soft biological tissue;

actuating the actuator to subject the measurement point on the surface of the skin to a preset pre-tension in a direction of the axis of movement of the testing end;

then actuating the actuator to subject the testing end to a brief mechanical impulse in the direction of the axis of movement of the testing end with quick release under constant pre-tension;

then registering, with the accelerometer in the form of an acceleration curve, a damped natural oscillation in response to the mechanical impulse;

performing signal processing on signals representing the acceleration during the damped natural oscillation to obtain values of the biomechanical and viscoelastic properties of the skin.

8. A method as claimed in claim 7, wherein the brief mechanical impulse has a duration less than 25 ms.

9. A method as claimed in claim 7, further comprising, after the actuating, monitoring the damped natural oscillation for up to 400 ms.

10. A method as claimed in claim 7, wherein the performing signal processing step comprises filtering out low and high frequencies that are not characteristic of the damped natural oscillation.

11. A method as claimed in claim 7, wherein the device further comprises a gravitational sensor, and a feedback circuit, and the method further comprises ensuring that the preset pre-tension and the brief mechanical impulse have values which are unaffected by an orientation of the housing relative to a gravitational field.

12. A method as claimed in claim 7, wherein the device further comprises a control circuit, wherein the accelerometer is arranged to provide a signal indicative of an inclination of the housing from a horizontal axis to the control circuit, and wherein the method further comprises compensating for the inclination from the horizontal axis.

* * * * *